United States Patent

Gonda et al.

[11] Patent Number: 6,070,575
[45] Date of Patent: Jun. 6, 2000

[54] AEROSOL-FORMING POROUS MEMBRANE WITH CERTAIN PORE STRUCTURE

[75] Inventors: Igor Gonda, San Francisco; Jeffrey A. Schuster, Oakland; Rajesh S. Patel, Fremont, all of Calif.

[73] Assignee: Aradigm Corporation, Hayward, Calif.

[21] Appl. No.: 09/192,833

[22] Filed: Nov. 16, 1998

[51] Int. Cl.$^7$ ................................................. A61M 15/00
[52] U.S. Cl. ............................. 128/203.12; 128/203.21
[58] Field of Search ...................... 128/203.12, 203.15, 128/203.23, 203.21, 200.14, 204.23; 222/95; 239/102, 2, 145; 604/58, 62

[56] References Cited

U.S. PATENT DOCUMENTS

| | | |
|---|---|---|
| 3,934,585 | 1/1976 | Maurice . |
| 4,508,749 | 4/1985 | Brannon et al. . |
| 4,677,975 | 7/1987 | Edgar et al. . |
| 5,497,763 | 3/1996 | Lloyd et al. ................ 128/200.14 |
| 5,497,944 | 3/1996 | Weston et al. . |
| 5,533,505 | 7/1996 | Kallstrand et al. ............ 128/203.15 |
| 5,544,646 | 8/1996 | Lloyd et al. . |
| 5,660,166 | 8/1997 | Lloyd et al. . |
| 5,718,222 | 2/1998 | Lloyd et al. . |
| 5,823,178 | 10/1998 | Lloyd et al. . |
| 5,829,435 | 11/1998 | Rubsamen et al. . |

FOREIGN PATENT DOCUMENTS

WO 96/06581 3/1996 WIPO .

*Primary Examiner*—Aaron J. Lewis
*Assistant Examiner*—Teena Mitchell
*Attorney, Agent, or Firm*—Karl Bozicevic; Bozicevic, Field & Francis LLP

[57] ABSTRACT

A nozzle comprised of a thin, flexible membrane material having a plurality of pores is disclosed. In one embodiment, the pores have an unflexed exit aperture diameter in the range of about 0.5 to about 2 microns (preferably about 1 micron) and are positioned substantially uniformly in the material, preferably about 50 microns apart. The nozzle preferably has a conical or trumpet-shaped cross-section. In another aspect of the invention, the exit aperture of the nozzle is surrounded by an elevated area protruding above the substantially planar exit side of the membrane in order to prevent intrusion of liquid back into the nozzle. The nozzle can be used to form an aerosol containing a pharmaceutical composition from the exit side of the nozzle upon forcible application of the composition to the entrance side of the nozzle. This aerosol can be used to administer the pharmaceutical composition, for example, to the eye or to a selected portion of the respiratory tract. The nozzle is preferably a component of a container which holds a formulation of drug.

24 Claims, 8 Drawing Sheets

AEROSOL-FORMING POROUS MEMBRANE WITH CERTAIN PORE STRUCTURE

BACKGROUND OF THE INVENTION

Aerosol therapy can be accomplished by aerosolization of a formulation (e.g., a drug formulation or diagnostic agent formulation) and inhalation of the aerosol. The formulation can be used to treat lung tissue locally and/or be absorbed into the circulatory system to deliver the drug systemically. Where the formulation contains a diagnostic agent, the formulation can be used for diagnosis of, for example, conditions and diseases associated with pulmonary dysfunction. In general, aerosolized particles for respiratory delivery must have a diameter of 12 microns or less. However, the preferred particle size varies with the site targeted (e.g, delivery targeted to the bronchi, bronchia, bronchioles, alveoli, or circulatory system). For example, topical lung treatment can be accomplished with particles having a diameter in the range of 0.01 to 12.0 microns. Effective systemic treatment requires particles having a smaller diameter, generally in the range of 0.5 to 6.0 microns, while effective ocular treatment is adequate with particles having a larger diameter, generally 15 microns or greater, generally in the range of 15–100 microns.

Generation of aerosolized particles and their respiratory delivery is generally accomplished by three distinct methodologies. One method uses a device known as a "metered dose inhaler" (MDI). Drugs delivered using an MDI are dispersed in a low boiling point propellant (e.g., a chlorofluorocarbon or hydrofluorocarbon) and loaded in a pressurized canister. A metered amount of the drug/propellant formulation is released from the MDI by activating a valve on the canister. The propellant "flashes" or quickly evaporates and particles of the drug are inhaled by the patient. Although MDIs provide a self-contained, easily portable device, the propellants have adverse environmental effects. In addition, it is difficult to reliably deliver a precise dosage of drug using an MDI. The patient frequently actuates the device at the incorrect point during the breathing cycle, or breathes at the wrong flow rate while inhaling the drug. Thus, patients may receive inconsistent doses, sometimes inspiring too little medication, other times taking a second dose after a partial failure and thereby receiving too much medication.

Breath actuated drug delivery devices, which attempt to overcome the dosing problems of MDIs, are activated to release a dose when the patient's inspiratory flow crosses a fixed threshold. However, the patient's inspiratory effort may not be sufficient to satisfy the threshold to trigger drug release. Or, although the patient's inspiration effort may be sufficient to release a metered dose, the inspired volume following the release may not be sufficient to cause the aerosol medication to pass into the desired portion of the patient's airways. Finally, whether breath-actuated or not, MDIs generate an aerosol that can contain particles of very different sizes. Larger particles are not delivered to the same site in the lung and/or at the same rate as the smaller particles in the aerosol. The production of an aerosol of varying particle size thus makes the delivery of a precise, reproducible dosage of medication or diagnostic agent to the desired regions of the respiratory tract extremely difficult if not impossible.

The second method for generation of aerosolized particles for respiratory delivery uses devices known as "dry powder inhalers" (DPI). DPIs typically use bursts of air to entrain small amounts of the drug, thus forming a dust cloud of dry drug particles. DPIs do not require the propellants of MNDIs. However, like MDIs, DPIs form aerosols composed of many different sizes of particles, making the delivery of a precise dose to a desired site in the respiratory tract difficult.

Nebulizers, devices used in a third method of respiratory drug delivery, utilize various means to create a fog or mist from an aqueous solution or suspension containing a pharmaceutically active drug. The mist created by the nebulizer device is directed towards the face of the patient and inhaled through the mouth and/or nose. The formulation delivered with nebulizers is sometimes diluted prior to delivery. The entire diluted formulation must generally be administered within a single dosing event in order to maintain the desired level of sterility.

Nebulizer devices can be quite useful when the precise dosing of the drug being delivered to the patient is not of particular importance, e.g., for treatment of a patient with a bronchodilator until he feels some improvement in lung function. When precise dosing is more important, the nebulizer device and delivery methodology suffers from many of the disadvantages of metered dose inhaler devices and methodology as described above. In addition, nebulizers generally are large and not easily transportable devices. Accordingly, a nebulizer can only be used within a fixed location such as the patient's home, the doctor's office and/or hospital. Yet another disadvantage of nebulizers is that they produce an aerosol which has a distribution of particle sizes, not all of which are of appropriate size to reach the targeted areas of the lung.

An aerosolization device can also be used to deliver treatment to the eye. Ophthalmic treatment fluids are commonly administered to the eye by means of eye drops or ointments. The use of eye drops has a number of disadvantages, primarily as a consequence of the difficulty with which drops are accepted by the patient. The drops are relatively large, and the instinctive blink that is provoked by the arrival of a drop on the eye severely limits the amount or proportion of fluid that actually contacts the target area of the eye. Typically less than 10% of a 50 $\mu$l drop reaches the desired site of administration, the remainder being lost by drainage, either externally or through nasolacrimal drainage. Such use of expensive treatment fluids leads to substantial uncertainty regarding the effectiveness of treatment. Ointments are associated with similar problems in their use to accomplish ocular therapy.

Various techniques for delivering treatment fluid to the eye are known. Most employ treatment systems in which treatment fluid is drawn from a reservoir and discharged in a controlled manner to the eye (see, e.g., WO96/06581). U.S. Pat. No. 3,934,585 disclosed a variety of mechanisms for delivering unit doses of treatment fluid to the human eye. For example, treatment fluid can be delivered by applying compressed air to one end of a tube resulting in the discharge of treatment fluid from the other end.

Devices and methods for controlling aerosol particle size are known in the art. For example, U.S. Pat. No. 4,926,852 described control of particle size by metering a dose of medication into a flow-through chamber that has orifices to limit the flow rate. U.S. Pat. No. 4,677,975 described a nebulizer device having baffles to remove particles above a selected size from an aerosol. U.S. Pat. No. 3,658,059 employed a baffle that changes the size of an aperture in the passage of the suspension being inhaled to select the quantity and size of suspended particles delivered. U.S. Pat. No. 5,497,944 described a method and device for generating an aerosol by passing the formulation through a small nozzle aperture at high pressure. However, devices that process the aerosol particle size after generation (e.g., by filtering the aerosol after it is formed from the formulation) are typically inefficient, wasteful, and/or require a substantially greater amount of force to generate the aerosol.

Co-owned U.S. Pat. No. 5,544,646 and U.S. patent applications Ser. Nos. 08/454,421, 08/630,391, 08/693,593 and 08/804,041 describe devices and methods useful in the generation of aerosols suitable for drug delivery. A drug formulation is forcibly applied to one side of the pore-containing membrane so as to produce an aerosol on the exit side of the membrane. Aerosols containing particles with a more uniform size distribution can be generated using such devices and methods, and can be delivered to particular locations within the respiratory tract.

One impediment to aerosol formation using prior membranes is the accumulation of a liquid layer on the exit side of the membrane. This can occur when forcible application of the formulation to the entrance side of the nozzle, rather than causing aerosolization, causes lateral spreading of liquid from the exit side, for example from poorly formed or irregular pores, or where the pressure is insufficient to consistently generate an aerosol. This liquid layer can spread to properly functioning pores and thereby disrupt their function, further degrading performance of the nozzle. This problem is particularly acute, for example, where the pores are closely or irregularly spaced, or where extrusion takes place over a significant period of time, or when the nozzle is to be used for repeated administration.

SUMMARY OF THE INVENTION

We have now invented an extrusion nozzle that is particularly well suited to extrusion of a formulation into the entraining airstream and delivery of particles having an improved size distribution to the respiratory tract. The nozzles of the invention maximize the conversion of pressure on the formulation container to kinetic energy of the formulation being extruded, and provide aerosol particles of the desired sizes.

One aspect of the invention is a nozzle for aerosolizing a formulation, said nozzle comprising a membrane having about 200 to about 1,000 holes, said holes having an average relaxed exit aperture diameter of from about 0.5 to about 1.5 $\mu$m and spaced from about 30 to about 70 $\mu$m apart from each other. The membrane is preferably flexible.

In a further aspect of the invention, a nozzle is provided wherein the area surrounding the exit aperture of the pores is elevated above the (otherwise substantially planar) exit side of the film so as to prevent intrusion of liquid into the exit aperture of the pores.

In another aspect of the invention, a nozzle is provided wherein the exit aperture of the pores has a smaller diameter than the entrance aperture.

In yet another aspect of the invention, a nozzle is provided wherein the pores are incompletely formed so that, upon administration of pressure to the entrance side of the film, the exit aperture is formed by bursting outward the exit side of the pores, thereby forming an elevated area preventing liquid intrusion into the exit aperture.

In a further aspect of the invention, a strip containing multiple nozzles is provided.

Another aspect of the invention is a method for aerosolizing a formulation in a way that maximizes the amount of formulation available for inhalation, comprising extruding the formulation into an airstream through a flexible, porous membrane, where the pores are from about 0.5 to about 1.5 microns in exit aperture diameter when unflexed, and are spaced about 30–70 $\mu$m apart.

Still another aspect of the invention is a method for aerosolizing a formulation through a nozzle comprising such pores where the area surrounding the exit aperture of the pores is elevated above the substantially planar exit side of the membrane.

Yet another aspect of the invention is a method for aerosolizing a formulation through pores having entrance apertures wider than their exit apertures.

DESCRIPTION OF THE PREFERRED EMBODIMENTS

Figure 1:
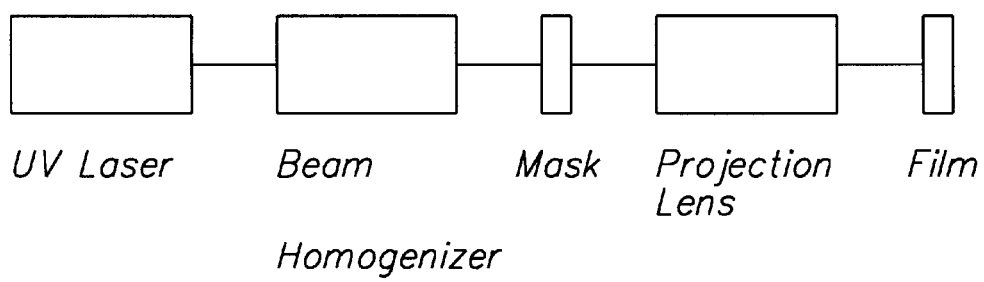
FIG. 1 is a schematic drawing of an excimer laser apparatus used to ablate pores in a material using the method of the invention.

Before the present methods of generating an aerosol and delivering an aerosolized formulation to a patient and devices, containers, and formulations used in connection with such are described, it is to be understood that this invention is not limited to the particular methodology, devices, containers and formulations described, as such methods, devices, containers and formulations may, of course, vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a," "an," and "the" include plural referents unless the context clearly dictates otherwise. Thus, for example, reference to "a formulation" includes mixtures of different formulations, reference to "an asthma attack" includes one or more of such events, and reference to "the method of treatment" and to "the method of diagnosis" includes reference to equivalent steps and methods known to those skilled in the art, and so forth.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller range is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the invention, the preferred methods and materials are now described. All publications mentioned herein are incorporated herein by reference to describe and disclose specific information for which the reference was cited.

The publications discussed above are provided solely for their disclosure prior to the filing date of the present application. Nothing herein is to be construed as an admission that the invention is not entitled to antedate such disclosure by virtue of prior invention.

DEFINITIONS

The terms "package" and "disposable package" are used interchangeably herein and shall be interpreted to mean a container or two or more containers linked together by an interconnecting means wherein each container preferably includes one or more channels which provide for fluid connection from the container to a nozzle comprised of a porous membrane, which nozzle is preferably not positioned directly over the container, and wherein each container includes at least one surface that is collapsible in a manner so as to allow the forced displacement of the contents of the container through a low resistance filter and out the nozzle (without rupturing the container) in a manner such that the contents are aerosolized. There are at least two variations of the package, depending on whether the drug can be stably stored in a liquid form or must be stored dry and combined with liquid immediately prior to aerosolization.

The contents of each container preferably comprises a formulation, preferably a flowable formulation, more preferably a liquid, flowable formulation, which includes a pharmaceutically active drug or a diagnostic agent. If the drug or diagnostic agent is not liquid and of a sufficiently low viscosity to allow the drug to be aerosolized, the drug or diagnostic agent is dissolved or dispersed in an excipient carrier, preferably without any additional material such as preservatives that might affect the patient. When the contents must be stored in a dry state, the package further includes another container that holds the liquid and can be combined with the dry drug immediately prior to administration.

The term "container" is used herein to mean a receptacle for holding and/or storing a drug formulation. The container can be single-dose or multidose, and/or disposable or refillable.

The term "cassette" shall be interpreted to mean a container which holds, in a protective cover, a package or a plurality of packages which packages are interconnected to each other and held in the cassette in an organized manner, e.g., interfolding or wound. The cassette is connectable to a dispensing device, which dispensing device may include a power source, e.g., one or more batteries which provide power to the dispensing device.

The term "porosity" is used herein to mean a percentage of an area of a surface area that is composed of open space, e.g., a pore, hole, channel or other opening, in a membrane, nozzle, filter or other material. The percent porosity is thus defined as the total area of open space divided by the area of the material, expressed as a percentage (multiplied by 100). High porosity (e.g., a porosity greater than 50%) is associated with high flow rates per unit area and low flow resistance. In general, the porosity of the nozzle is less than 10%, and can vary from $10^{-3}\%$ to 10%, while the porosity of the filter is at least 1%, and preferably it is at least 50% porous.

The term "porous membrane" shall be interpreted to mean a membrane of material having any given outer parameter shape, but preferably having a convex shape, wherein the membrane has a plurality of pores therein, which openings may be placed in a regular or irregular pattern, and which pores have an unflexed diameter of their exit aperture in the range of 0.25 micron to 6 microns and a pore density in the range of 1 to 1,000 pores per square millimeter for respiratory delivery. For ocular delivery, the pores have an unflexed diameter of their exit aperture in the range of 5 microns to 50 microns, preferably 7.5 to 25 microns, and a similar pore density. The porous membrane has a porosity of about 0.0005% to 0.2%, preferably about 0.01% to 0.1%. In one embodiment, the porous membrane comprises a single row of pores on, e.g., a large piece of membrane material. The pores may be planar with respect to the surface of the porous membrane material, or may have a conical configuration. The membrane material is preferably hydrophobic and includes materials such as polycarbonates, polyimides, polyethers, polyether imides, polyethylene and polyesters which may have the pores formed therein by any suitable method including laser drilling or anisotropic etching through a thin film of metal or other suitable material. The membrane preferably has sufficient structural integrity so that it is maintained intact (will not rupture) when subjected to force in the amount up to about 40 bar, preferably of up to about 50 bar while the formulation is forced through the pores.

The term "low resistance filter" shall be interpreted to mean a filter of material having any given outer parameter shape, and having a plurality of openings therein, which openings may be placed in a regular or irregular pattern. The openings in the filter can be of any shape, and are preferably substantially evenly distributed throughout the filter surface area. Preferably, the porosity of the low resistance filter is greater than 50%, preferably at least 60%, more preferably at least 70%. Preferably, the low resistance filter prevents passage of particles greater than about 0.5 microns in size (e.g., having a diameter greater than 0.5 microns). Where the filter openings are pores, the pores can have a diameter in the range of from about 0.25 micron to 6 microns for respiratory tract delivery, or from about 5 microns to 50 microns for ocular delivery. The filter has an opening density in the range of from about 10 to 20,000,000 openings per mm². Preferably the filter has holes of about 0.5 μm positioned about 0.5 μm apart at a density of $10^6$ holes per mm². Preferably, the ratio of the pore density of the porous membrane to the low resistance filter is in the range of about 1:1.5 to about 1:100,000; the ratio of the pore diameter of the pores of the porous membrane to the diameter of the openings of the low resistance filter is in the range of from about 1:0.95 to 1:0.1. Preferably, the flow resistance of the filter is the same as or lower than the flow resistance of the porous membrane used in conjunction with the filter. The filter is preferably comprised of a material having a density in the range of 0.25 to 3.0 mg/cm², more preferably 1.7 mg/cm², and a thickness of about 10 microns to about 500 microns, more preferably about 20 to 150 microns. The filter can be made of any material suitable for use in the invention, e.g., cellulose ester, mixed cellulose ester, modified polyvinylidene fluoride, polytetrafluoroethylene, bisphen polycarbonate, borosilicate glass, silver, polypropylene, polyester, polyimide, polyether, or any suitable polymeric material. The filter material includes materials such as polycarbonates and polyesters which may have the pores formed therein by any suitable method, including anisotropic etching or by etching through a thin film of metal or other suitable material, electron discharge machining, or laser micromachining. The filter preferably has sufficient structural integrity such that it is maintained intact (i.e., will not rupture) when subjected to force up to about 40 bar, preferably up to about 50 bar during extrusion of the formulation through the pores (of filter or membrane). The porosity of the low resistance filter is 5–85%, preferably 70%, while the porosity of the nozzle is $10^{-4}\%$–1%, preferably 0.001%–0.1%.

The term "flow resistance" shall be interpreted to mean the resistance associated with the passage of a liquid or aerosol through a porous material, e.g., through the porous membrane or the low resistance filter described herein. Flow resistance is affected by the size and density of pores in the porous material, the viscosity of a liquid passing through the material, and other factors well known in the art. In general, "low resistance" of the "low resistance filter" means that the flow resistance of the low resistance filter is substantially the same as or less than the flow resistance of the porous membrane used in conjunction with the low resistance filter.

The terms "drug", "active agent", "pharmaceutically active drug" and the like are used interchangeably herein to encompass compounds which are administered to a patient in order to obtain a desired pharmacological effect. The effect may be a local or topical effect in the eye or respiratory tract such as in the case of most respiratory or ophthalmic drugs or may be systemic as with analgesics, narcotics, hormones, hematopoietic drugs, various types of peptides including insulin and hormones such as EPO. Other exemplary drugs are set forth in U.S. Pat. No. 5,419,315, issued May 30, 1995, PCT Published Application WO 96/13291, published May 9, 1996, and PCT Published Application WO 96/13290, published May 9, 1996, incorporated herein by reference.

The term "respiratory drug" shall be interpreted to mean any pharmaceutically effective compound used in the treatment of any respiratory disease and in particular the treatment of diseases such as asthma, bronchitis, emphysema and cystic fibrosis. Useful "respiratory drugs" include those which are listed within the Physician's Desk Reference (most recent edition). Such drugs include beta adrenergic agonists which include bronchodilators including albuterol, isoproterenol sulfate, metaproterenol sulfate, terbutaline sulfate, pirbuterol acetate, salmeterol xinotoate, formoterol; steroids including corticosteroids used as an adjunct to beta agonist bronchodilators such as beclomethasone dipropionate, flunisolide, fluticasone, budesonide and triamcinolone acetonide; antibiotics including antifungal and antibacterial agents such as chloramphenicol, chlortetracycline, ciprofloxacin, framycetin, fusidic acid, gentamicin, neomycin, norfloxacin, ofloxacin, polymyxin, propamidine, tetracycline, tobramycin, quinolines, and the like; and also includes peptide nonadrenergic noncholinergic neurotransmitters and anticholinergics. Antiinflammatory drugs used in connection with the treatment of respiratory diseases include steroids such as beclomethasone dipropionate, triamcinolone acetonide, flunisolide and fluticasone. Other antuinflammatory drugs and antiasthmatics which include cromoglycates such as cromolyn sodium. Other respiratory drugs which would qualify as bronchodilators include anticholinergics including ipratropium bromide. Other useful respiratory drugs include leukotriene (LT) inhibitors, vasoactive intestinal peptide (VIP), tachykinin antagonists, bradykinin antagonists, endothelin antagonists, heparin furosemide, antiadhesion molecules, cytokine modulators, biologically active endonucleases, recombinant human (rh) DNase, $\alpha_1$ antitrypsin and antibiotics such as gentamicin, tobramycin, cephalosporins or penicillins, nucleic acids and gene vectors. The present invention is intended to encompass the free acids, free bases, salts, amines and various hydrate forms including semihydrate forms of such respiratory drugs and is particularly directed towards pharmaceutically acceptable formulations of such drugs which are formulated in combination with pharmaceutically acceptable excipient materials generally known to those skilled in the art—preferably without other additives such as preservatives. Preferred drug formulations do not include additional components such as preservatives which have a significant effect on the overall formulation. Thus preferred formulations consist essentially of pharmaceutically active drug and a pharmaceutically acceptable carrier (e.g., water and/or ethanol). However, if a drug is liquid without an excipient the formulation may consist essentially of the drug provided that it has a sufficiently low viscosity that it can be aerosolized using a dispenser of the present invention.

The term "ophthalmic drug" or "ophthalmic treatment fluid" refers to any pharmaceutically active compound used in the treatment of any ocular disease. Therapeutically useful compounds include, but are not limited to, (1) antiglaucoma compounds and/or compounds that decrease intraocular pressure such as β-adrenoceptor antagonists (e.g., cetamolol, betaxolol, levobunolol, metipranolol, timolol, etc.), mitotics (e.g., pilocarpine, carbachol, physostigmine, etc.), sympatomimetics (e.g., adrenaline, dipivefrine, etc.), carbonic anhydrase inhibitors (e.g., acetazolamide, dorzolamide, etc.), prostaglandins (e.g., PGF-2 alpha), (2) antimicrobial compounds including antibacterial and antifungal compounds (e.g., chloramphenicol, chlortetracycline, ciprofloxacin, framycetin, fusidic acid, gentamicin, neomycin, norfloxacin, ofloxacin, polymyxin, propamidine, tetracycline, tobramycin, quinolines, etc.), (3) antiviral compounds (e.g., acyclovir, cidofovir, idoxuridine, interferons, etc.), (4) aldose reductase inhibitors (e.g., tolrestat, etc.), (5) antiinflammatory and/or antiallergy compounds (e.g., steroidal compounds such as betamethasone, clobetasone, dexamethasone, fluorometholone, hydrocortisone, prednisolone, etc. and nonsteroidal compounds such as antazoline, bromfenac, diclofenac, indomethacin, lodxamide, saprofen, sodium cromoglycate, etc., (6) artificial tear/dry eye therapies, comfort drops, irrigation fluids, etc. (e.g., physiological saline, water, or oils; all optionally containing polymeric compounds such as acetylcysteine, hydroxyethylcellulose, hydroxymellose, hyaluronic acid, polyvinyl alcohol, polyacrylic acid derivatives, etc.), (7) local anaesthetic compounds (e.g., amethocaine, lignocaine, oxbuprocaine, proxymetacaine, etc.), (8) compounds which assist in the healing of corneal surface defects (e.g., cyclosporine, diclofenac, urogastrone and growth factors such as epidermal growth factor), (9) mydriatics and cycloplegics (e.g., atropine, cyclopentolate, homatropine, hyoscine, tropicamide, etc.), (10) compounds for the treatment of pterygium (e.g., mitomycin C., collagenase inhibitors such as batimastat, etc.), (11) compounds for the treatment of macular degeneration and/or diabetic retinopathy and/or cataract prevention, (12) compounds for systemic effects following absorption into the bloodstream after ocular administration (e.g., insulin, narcotics, analgesics, anesthetics).

The terms "diagnostic" and "diagnostic agent" and the like are used interchangeably herein to describe any compound that is delivered to a patient in order to carry out a diagnostic test or assay on the patient. Such agents are often tagged with a radioactive or fluorescent component or other component which can be readily detected when administered to the patient. Exemplary diagnostic agents include, but are not limited to, methacholine, histamine, salt, specific allergens (such as pollen or pollen extracts), sulphites, and imaging agents for magnetic resonance imaging and/or scintigraphy. Diagnostic agents can be used to, for example, assess bronchial constriction in patients having or suspected of having cystic fibrosis or asthma. Radiolabelled aerosols can be used to diagnose pulmonary embolism, or to assess mucociliary clearance in various chronic obstructive diseases of the lung. Diagnostic agents can also be used to assess ophthalmic conditions. Exemplary ocular diagnostic agents include, but are not limited to, such compounds as fluorescein or rose bengal.

The term "formulation" is intended to encompass any drug or diagnostic agent formulation which is delivered to a patient using the present invention. Such formulations generally include the drug or diagnostic agent present within a pharmaceutically acceptable inert carrier. The formulation is generally in a liquid flowable form which can be readily aerosolized, the particles having a particle size in the range of 0.5 to 12 microns in diameter for respiratory administration. Formulations can be administered to the patient using device of the invention can be administered by nasal, intrapulmonary, or ocular delivery.

The terms "aerosol," "aerosolized formulation," and the like, are used interchangeably herein to describe a volume of air which has suspended within it particles of a formulation comprising a drug or diagnostic agent wherein the particles have a diameter in the range of 0.5 to 12 microns, for respiratory therapy, or in the range of 15 to 50 microns for ocular therapy.

The term "aerosol-free air" is used to describe a volume of air which is substantially free of other material and, in particular, substantially free of particles of respiratory drug.

The term "dosing event" shall be interpreted to mean the administration of drug or diagnostic agent to a patient by the ocular or respiratory (e.g., nasal or intrapulmonary) route of administration (i.e., application of a formulation to the patient's eye or to the patient's respiratory tract by inhalation of aerosolized particles) which event may encompass one or more releases of drug or diagnostic agent formulation from a dispensing device over a period of time of 15 minutes or less, preferably 10 minutes or less, and more preferably 5 minutes or less, during which period multiple administrations (e.g., applications to the eye or inhalations) may be made by the patient and multiple doses of drug or diagnostic agent may be released and administered. A dosing event shall involve the administration of drug or diagnostic formulation to the patient in an amount of about 10 $\mu$l to about 1,000 $\mu$l in a single dosing event. Depending on the drug concentration in the formulation, a single package may not contain sufficient drug for therapy or diagnosis. Accordingly, a dosing event may include the release of drug or diagnostic agent contained from several containers of a package held in a cassette or the drug or diagnostic agent contained within a plurality of such containers when the containers are administered over a period of time, e.g., within 5 to 10 minutes of each other, preferably within 1–2 minutes of each other.

The term "velocity of the drug" or "velocity of particles" shall mean the average speed of particles of drug or diagnostic agent formulation moving from a release point such as the porous membrane of the nozzle or a valve to a patient's mouth or eye. In a preferred embodiment pertaining to respiratory therapy, the relative velocity of the particles is zero or substantially zero with reference to the flow created by patient inhalation.

The term "bulk flow rate" shall mean the average velocity at which air moves through a channel.

The term "flow boundary layer" shall mean a set of points defining a layer above the inner surface of a channel through which air flows wherein the air flow rate below the boundary layer is substantially below the bulk flow rate, e.g., 50% or less than the bulk flow rate.

The term "carrier" shall mean a flowable, pharmaceutically acceptable excipient material, preferably a liquid, flowable material, in which a drug or diagnostic agent is suspended in or more preferably dissolved in. Useful carriers do not adversely interact with the drug or diagnostic agent and have properties which allow for the formation of aerosolized particles, which particles preferably have a diameter in the range of 0.5 to 12.0 microns that are generated by forcing a formulation comprising the carrier and drug or diagnostic agent through pores having an unflexed diameter of 0.25 to 6.0 microns for delivery to the respiratory tract. Similarly, a useful carrier for delivery to the eye does not adversely interact with the drug or diagnostic agent and has properties which allow for the formation of aerosolized particles, which particles preferably have a diameter of 15 to 50 microns and are generated by forcing the formulation comprising the carrier and drug or diagnostic agent through pores 7.5 to 25 microns in relaxed diameter. Preferred carriers include water, ethanol, saline solutions and mixtures thereof, with pure water being preferred. Other carriers can be used provided that they can be formulated to create a suitable aerosol and do not adversely affect human tissue or the drug or diagnostic agent to be delivered.

The term "measuring" describes an event whereby the (1) total lung capacity, (2) inspiratory flow rate or (3) inspiratory volume of the patient is measured and/or calculated and the information used in order to determine an optimal point in the inspiratory cycle at which to release an aerosolized and/or aerosol-free volume of air. An actual measurement of both rate and volume may be made or the rate can be directly measured and the volume calculated based on the measured rate. The total lung capacity can be measured or calculated based on the patient's height, sex and age. It is also preferable to continue measuring inspiratory flow during and after any drug delivery and to record inspiratory flow rate and volume before, during and after the release of drug. Such reading makes it possible to determine if drug or diagnostic agent was properly delivered to the patient.

The term "monitoring" shall mean measuring lung functions such as inspiratory flow, inspiratory flow rate, and/or inspiratory volume so that a patient's lung function as defined herein, can be evaluated before and/or after drug delivery thereby making it possible to evaluate the effect of drug delivery on, for example, the patient's lung function.

The term "inspiratory flow profile" shall be interpreted to mean data calculated in one or more events measuring inspiratory flow and cumulative volume, which profile can be used to determine a point within a patient's inspiratory cycle which is optimal for the release of drug to be delivered to a patient. An optimal point within the inspiratory cycle for the release of an aerosol volume is based, in part, on (1) a point most likely to deliver the aerosol volume to a particular area of a patient's respiratory tract, in part on (2) a point within the inspiratory cycle likely to result in the maximum delivery of drug and, in part, on (3) a point in the cycle most likely to result in the delivery of a reproducible amount of drug to the patient at each release of drug. The criteria 1–3 are listed in a preferred order of importance. However, the order of importance can change based on circumstances. The area of the respiratory tract being treated is determined by adjusting the volume of aerosol-containing or aerosol-free air and/or by adjusting the particle size of the aerosol. The repeatability is determined by releasing at the same point in the respiratory cycle each time drug is released. To provide for greater efficiency in delivery, the drug delivery point is selected within given parameters.

The terms "formulation" and "flowable formulation" and the like are used interchangeably herein to describe any pharmaceutically active drug (e.g., a respiratory drug, or drug that acts locally or systemically, and that is suitable for respiratory delivery) or diagnostic agent combined with a pharmaceutically acceptable carrier in flowable form having properties such that it can be aerosolized to particles having a diameter of 0.5 to 12.0 microns for respiratory therapy, or 15 to 75 microns for ocular therapy. Such formulations are preferably solutions, e.g., aqueous solutions, ethanolic solutions, aqueous/ethanolic solutions, saline solutions, colloidal suspensions and microcrystalline suspensions. Preferred formulations are drug(s) and/or diagnostic agent(s) dissolved in a liquid, preferably in water.

The term "substantially dry" shall mean that particles of formulation include an amount of carrier (e.g., water or ethanol) which is equal to (in weight) or less than the amount of drug or diagnostic agent in the particle, more preferably it means free water is not present.

The terms "aerosolized particles" and "aerosolized particles of formulation" shall mean particles of formulation comprised of carrier and drug and/or diagnostic agent that are formed upon forcing the formulation through a nozzle, which nozzle comprises a flexible porous membrane. Where respiratory therapy is desired, the particles are of a sufficiently small size such that when the particles are formed, they remain suspended in the air for a sufficient amount of time for inhalation by the patient through his nose or mouth. Where ocular therapy is desired, the particles formed are of a size optimal for application to the eye. Preferably, particles for respiratory delivery have a diameter of from about 0.5 micron to about 12 microns, and are generated by forcing the formulation through the pores of a flexible porous membrane, where the pores have an unflexed exit aperture diameter in the range of about 0.25 micron to about 6.0 microns. More preferably, the particles for respiratory delivery have a diameter of about 1.0 to 8.0 microns with the particles created by being moved through pores having an unflexed exit aperture diameter of about 0.5 to about 4 microns. For ocular delivery, the particles have a diameter from about 15 micron to about 75 microns, and are generated by forcing the formulation through the pores of a flexible porous membrane, where the pores have an unflexed exit aperture diameter in the range of about 5 micron to about 50 microns. More preferably, the particles for ocular delivery have a diameter of about 15 to 50 microns, and can be generated by forcing the formulation through flexible membrane pores having an unflexed exit aperture diameter of about 7.5 to about 25 microns. In either respiratory or ocular delivery, the flexible membrane pores are present at about 10 to 10,000 pores over an area in size of from about 1 sq. millimeter to about 1 sq. centimeter, preferably from about $1 \times 10^1$ to about $1 \times 10^4$ pores per square millimeter, more preferably from about $1 \times 10^2$ to about $3 \times 10^4$ pores per square millimeter, and the low resistance filter has an opening density in the range of 20 to 1,000,000 pores over an area of about one square millimeter.

The term "substantially through" with reference to the pores being formed in the membrane or material shall mean pores which either completely traverse the width of the membrane or are formed to have a thin peelable layer over their exit aperture. The pores formed with a peelable layer over their exit apertures are formed so as to peel outward at a substantially lower pressure than would be required to rupture the membrane in the nonporous areas.

GENERAL OVERVIEW OF THE METHODOLOGY OF THE INVENTION

The invention provides a means to deliver any type of drug or diagnostic agent to a patient by ocular administration or inhalation in the form of an aerosol having a desired aerosol particle size and having substantially no undesirable particles within the aerosol that would substantially affect the accuracy of the dose of drug or diagnostic agent delivered in the aerosol. The method of generating an aerosol according to the invention provides a means to generate a reproducible desirable dose of aerosol for therapeutic and diagnostic applications. Moreover, certain embodiments of the devices and methodology used do not require the release of low boiling point propellants in order to aerosolize drug, which propellants are conventionally used in connection with hand-held metered dose inhalers. However, like conventional hand-held metered dose inhalers, the devices used in conjunction with the present invention can be hand-held, self-contained, highly portable devices which provide a convenient means of delivering drugs or diagnostic agents to a patient via the respiratory route.

In general, an aerosol for respiratory or ocular delivery is generated from a drug or diagnostic agent formulation, preferably a flowable formulation, more preferably a liquid, flowable formulation. The drug or diagnostic agent formulation can be contained within a multidose container or within a container portion of a disposable package, where the container of the disposable package has at least one surface that is collapsible. The aerosol is generated by applying pressure of 50 bar or less, preferably 40 bar or less, to the collapsible container surface, thereby forcing the contents of the container through a low resistance filter and then through a nozzle comprised of a porous membrane. The porous membrane may be rigid or flexible. Preferably the porous membrane is flexible so that upon application of the pressure required to aerosol the formulation (i.e., preferably 50 bar or less, more preferably 40 bar or less), the nozzle's porous membrane becomes convex in shape, thus delivering the aerosolized drug or diagnostic agent into the flow path of the delivery device in a region beyond the flow boundary layer. The low resistance filter has a porosity the same as or preferably greater than the porosity of the porous membrane to provide for an overall flow resistance that is much lower than the flow resistance of the nozzle. The low resistance filter thus prevents particles of an undesirable size from reaching the nozzle, thereby lessening clogging of the nozzle from the inside, and filters out such undesirable particles before the aerosol for delivery is generated, thereby avoiding delivery of undesirable particles to the patient.

The formulations for use in the present invention can include preservatives or bacteriostatic type compounds. However, the formulation preferably comprises a pharmaceutically active drug (or a diagnostic agent) and pharmaceutically acceptable carrier such as water. The formulation can be primarily or essentially composed of the drug or diagnostic agent (i.e., without carrier) if the drug or diagnostic agent is freely flowable and can be aerosolized. Useful formulations can comprise formulations currently approved for use with nebulizers or for injections.

Further, the dispensing device of the present invention, which can be used to dispense a drug or diagnostic agent formulation according to the method of the invention, preferably includes electronic and/or mechanical components which eliminate direct user actuation of drug release. More specifically, where the device is used in respiratory therapy, the device preferably includes a means for measuring inspiratory flow rate and inspiratory volume and sending an electrical signal as a result of the simultaneous measurement of both (so that drug or diagnostic agent can be released at a preprogrammed optimal point) and also preferably includes a microprocessor which is programmed to receive, process, analyze and store the electrical signal of the means for measuring flow and upon receipt of signal values within appropriate limits sending an actuation signal to the mechanical means which causes drug (or diagnostic agent) to be extruded from the pores of the nozzle's porous membrane. Thus, since preferred embodiments of the devices used in connection with the present invention include a means of analyzing breath flow and a microprocessor capable of making calculations based the inhalation profile, the present invention can provide a means for repeatedly (1) dispensing and (2) delivering the same amount of the drug or diagnostic agent to a patient at each dosing event.

The nozzles of the invention preferably take the form of small pores in a thin membrane. The material used may be any material from which suitable pores can be formed and which does not adversely interact with other components of the delivery device, particularly with the formulation being administered. In a preferred embodiment, the material is a flexible polymeric organic material, for example a polyether, polycarbonate, polyimide, polyether imide, polyethylene or polyester. Flexibility of the material is preferred so that the nozzle can adopt a convex shape and protrude into the airstream upon application of pressure, thus forming the aerosol away from the static boundary layer of air. The membrane is preferably about 10 to about 100 $\mu$m in thickness, more preferably from about 12 to about 45 $\mu$m in thickness. A preferred material is a 25 $\mu$m thick film of polyimide. Considerations for the membrane material include the ease of manufacture in combination with the formulation container, flexibility of the membrane, and the pressure required to generate an aerosol from pores spanning a membrane of that thickness and flexibility.

Where a laser source is used to ablate the pores in the membrane, the particular laser source used will to some extent be determined by the material in which the pores are to be formed. Generally, the laser source must supply a sufficient amount of energy of a wavelength which can form an effective aerosolization nozzle in the material being ablated. Typically the wavelength can be from about 250 to about 360 nm.

The output of the particular laser source can be manipulated in a variety of ways prior to being applied to the material. For example, the frequency can doubled or tripled using, for example, a lithium triborate crystal or series of crystals using a type I process, a type II process or a combination thereof. This laser beam can be further split into multiple beams to create multiple pores simultaneously. The beam can also be directed through a mask or spatially filtered, and can also be expanded prior to focusing.

One laser effective for such nozzles is a neodymium-yttrium aluminum garnet laser. This laser is a pulsed ultraviolet wavelength light source which provides sufficiently high peak power in short pulses to permit precise ablation in a thin material. The beam profile from this laser is radially symmetric which tends to produce radially symmetric pores.

Another laser effective for creating pores in materials such as polyethers and polyimide is an excimer laser. This laser produces ultraviolet wavelength light, similar to the Nd:YAG laser. However, the beam is not radially symmetrical but can be projected through a mask to simultaneously drill one or more conical or cylindrical holes. Preferably, the laser source is an excimer laser providing a wavelength of 308 nm. The energy density used for such a laser typically ranges from about 525 to about 725 mJ/cm$^2$, and is preferably about 630 mJ/cm$^2$. Using such a laser on a 25 $\mu$m thick polyimide membrane, the number of pulses is typically about 100 to about 200.

For respiratory delivery, the pores are formed so as to have an unflexed exit aperture diameter from about 0.5 to about 6 $\mu$m, preferably about 1–2 $\mu$m. For ocular delivery, the pores are formed so as to have an unflexed exit aperture diameter in the range of 5 microns to 50 microns, preferably 7.5 to 25 microns. The pores can be spaced from about 10 to about 1000 $\mu$m apart or more, but are preferably spaced from about 30 to about 70 $\mu$m apart, most preferably about 50 $\mu$m apart. The pore spacing is determined in part by the need to prevent the aerosol from adjacent pores from adversely interfering with each other, and in part to minimize the amount of membrane used and the associated manufacturing difficulties and costs. The pore spacing is preferably fairly uniform, with a variability in the interpore distance of preferably less than about 20%, more preferably less than about 10%, and most preferably about 2% or less (<1 $\mu$m variability for pores spaced 50 $\mu$m apart).

The pores may be roughly cylindrical or conical in shape, where "cylindrical" means that the pores pass perpendicularly through the membrane and have approximately the same diameter on each surface of and throughout the membrane, and "conical" means that the pores are larger on one side of the membrane than on the other side, and includes instances where the cross-section of the pores is conical, curved or where the diameter of the pore is reduced stepwise. Preferably, the pores are conical. When the pores are conical, the wider diameter of the cone is found on the entrance side of the pore to which the formulation is applied under pressure, while the smaller diameter of the cone is found on the exit side of the pore from which aerosolization occurs. For example, for respiratory delivery, when the exit aperture of the holes is about 0.6 to about 1.5 $\mu$m in diameter, the entrance aperture preferably has a diameter of from about 4 to about 12 $\mu$m, more preferably from about 6 to about 12 $\mu$m. The aperture size is preferably uniform; following the methods taught herein, the variability in diameter of each hole having a 1.25 µm aperture is no more than 0.05 µm, and for a 6 lm aperture is no more than 0.1 µm. The nozzle may be provided as an integral part of the formulation packaging, or may be provided separately, for example integrally with the inhalation device, or wound on a roll for disposable use.

In an alternative embodiment, the pores are incompletely formed so that a thin peelable layer remains covering the exit apertures of the pores. This peelable layer bursts outward upon forcible application of the drug formulation to the nozzle during drug delivery, permitting aerosolization of the formulation. The peelable layer of the pores is formed so as to have a breaking pressure significantly below that of the overall membrane, and the pressure at which the layer bursts is significantly below that applied in the normal course of drug administration, so that the pores burst substantially uniformly and completely. The incompletely formed pores may be formed by application of a thin layer of material to the outer side of the membrane after formation of complete pores, or by incompletely ablating holes through the membrane.

Any number of pores may be formed in the material comprising the nozzle apparatus. The number of nozzles is determined in part by the amount of formulation which must be delivered for a given application, and therefore the potency and concentration of the agent being administered must be taken into account. Additionally, the period of time over which the formulation is to be administered must also be considered. In one embodiment of the invention, the pores are formed in a 7×48 array of pores spaced 50 µm apart. For a given pore exit diameter and formulation pressure, hole number can be adjusted to control delivery time. For example, if the expression $N=356*d^{-0.667}$ is used, the pressure required for a 1.2 second delivery time at each hole size will give robust aerosol generation.

Figure 2:
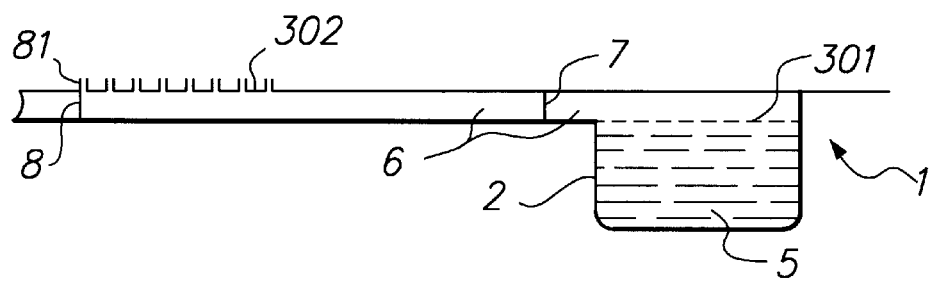
FIG. 2 is a cross-sectional view of a preferred embodiment of a container used in carrying out the invention, showing elevated areas surrounding the exit apertures of the nozzle pores.

In another embodiment, the pores are provided with elevated areas surrounding the exit aperture, so as to prevent liquid from intruding from the outer surface of the membrane back into the pore and thereby disrupting aerosolization. The elevated areas may be of any shape, such as circular or rectangular, or may be irregularly shaped. The elevated areas can be constructed by any suitable means, for example by etching away portions of the outer layer of the membrane, by laser drilling procedures which lead to sputtering of material around the pores, by molding or casting, by deposition of material via a mask in locations where pores are to be formed, and the like. FIG. 2 shows an example of a pore formed so as to have an elevated area via excimer laser ablation from the opposite side of the membrane. The formation of the elevated area via excimer laser ablation can be controlled by altering the pulse number: a minimal number of pulses used to penetrate the membrane will form an elevated area around the aperture on the opposite side of the membrane; increasing the number of pulses will then remove this elevated area. For example, for a 25 micron thick polyimide membrane, 120 pulses of a 308 nm excimer laser at an energy density of 630 mJ/cm² will form a pore having an elevated area, while increasing the number of pulses above 150 will remove the elevated area and slightly widen the pore aperture. The elevated areas may be of any suitable dimensions, but preferably extend significantly less than the interpore distance so as to provide lower areas where fluid is sequestered. The elevated areas can be made from any suitable material, for example the material comprising the bulk of the membrane, or may be made from materials with desirable properties such as hydrophobicity or solvent or drug repellence so as to repel the drug formulation from entering the exit aperture of the pores.

LOW RESISTANCE FILTER, NOZZLE, AND CONTAINER CONFIGURATIONS:

In general, the low-resistance filter and nozzle comprised of a porous membrane according to the invention can be used in conjunction with any container suitable for containing a drug or diagnostic agent formulation of interest. The container can be, for example, a single-dose container or a multidose container. The containers can be refillable, reusable, and/or disposable. Preferably, the container is disposable. The container can be designed for storage and delivery of a drug or diagnostic agent that is dry, substantially dry, liquid, or in the form of a suspension. The container may be any desired size. In most cases the size of the container is not directly related to the amount of drug or diagnostic agent being delivered in that most formulations include relatively large amounts of excipient material, e.g., water or a saline solution. Accordingly, a given size container could include a wide range of different doses by varying drug (or diagnostic agent) concentration.

The container can also be one that provides for storage of a drug or diagnostic agent in a dry or substantially dry form until the time of administration, at which point, if desired, the drug or diagnostic agent can be mixed with water or other liquid. An exemplary dual compartment container for carrying out such mixing of dry drug with liquid just prior to administration is described in copending U.S. application Ser. No. 08/549,295, filed Oct. 27, 1995, incorporated herein by reference with respect to such containers.

In a preferred embodiment, the containers useful with the invention comprise a single-use, single-dose, disposable container that holds a formulation for delivery to a patient and has a collapsible wall. In addition, the container can be configured in the same package with a porous membrane and a low resistance filter, where the low resistance filter is positioned between the porous membrane and a formulation contained in the container. The container is preferably disposable after a single use in the delivery of the formulation contained therein.

FIG. 2 is a cross-sectional view of a preferred embodiment of a disposable container 1 comprising the porous membrane of the invention. The container is shaped by a collapsible wall 2. The container 1 has an opening covered by a nozzle 302 comprised of a flexible porous membrane. The exit apertures of the pores of the nozzle are surrounded by elevated areas 81 which prevent intrusion of fluid back into the pores. The container 1 includes an opening which leads to an open channel 6 which channel 6 includes an abutment (or peelable seal) 7 which is peeled open upon the application of force created by formulation 5 being forced from the container. A low resistance filter 301 can be positioned between the formulation 5 and the peelable seal 7. The filter 301 has a porosity such that the presence of the filter 301 does not substantially increase the pressure required to generate an aerosol by forcing the formulation through the porous membrane of the nozzle. When the abutment 7 is peeled open, the formulation 5 flows to an area adjacent to the nozzle's flexible porous membrane 3 and is prevented from flowing further in the channel 6 by a nonbreakable abutment 8.

Figure 3:
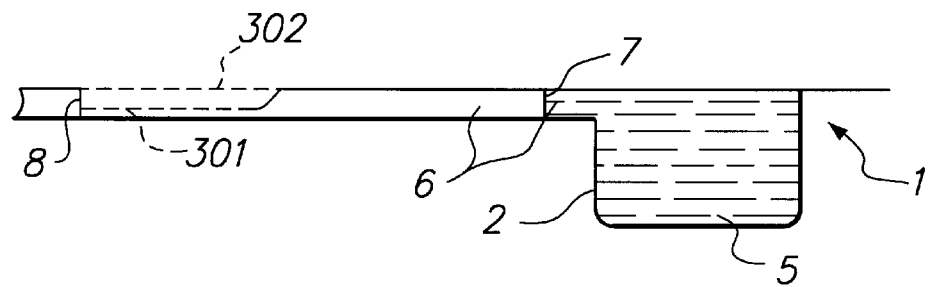
FIG. 3 is a cross-sectional view of a container of a preferred embodiment of a container used in carrying out the invention.
Figure 4:
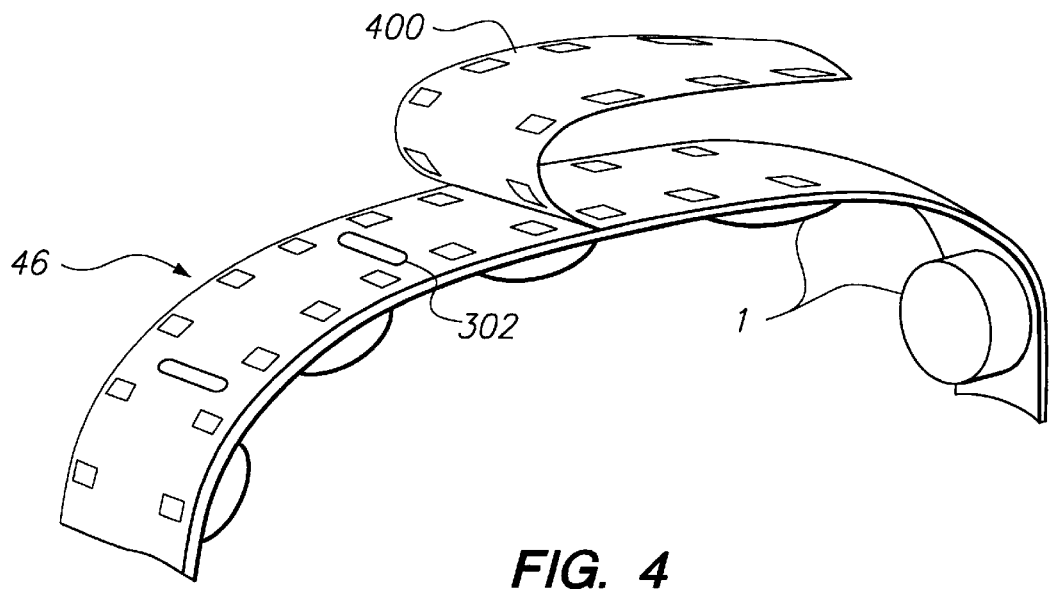
FIG. 4 is a top plan view of a disposable package of the invention.
Figure 5:
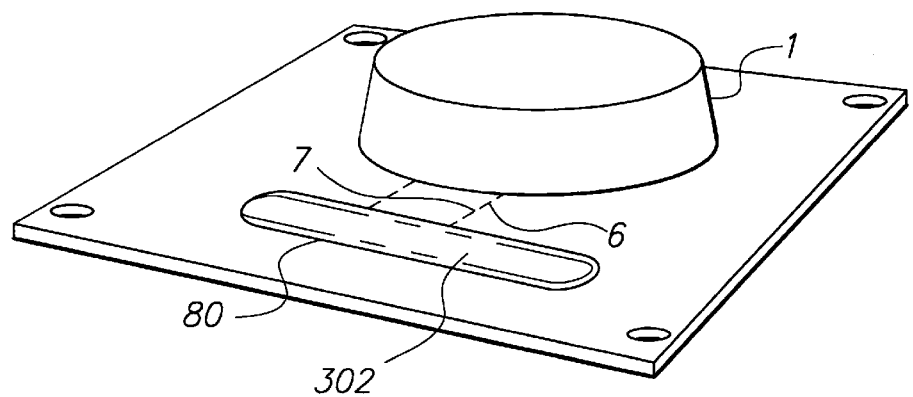
FIG. 5 is a cross-sectional view of a portion of a disposable package of the invention.

FIG. 3 is a cross-sectional view of another preferred embodiment of a disposable container 1 of the invention. The container is shaped by a collapsible wall 2. The container 2 includes an opening which leads to an open channel 6, which channel 6 includes an abutment (or peelable seal) 7 which is peeled open upon the application of force created by formulation 5 being forced from the container. The low resistance filter 301 is positioned between the peelable seal 7 and the nozzle 302. When the peelable seal 7 is broken, the formulation 5 flows to an area adjacent the low resistance filter 301, through the low resistance filter 301, if present, and out the nozzle 302 to form an aerosol. The formulation 5 is prevented from flowing further in the channel 6 by a nonbreakable abutment 8. A number of containers can be connected together to form a package 46 as shown in FIG. 4. The package 46 is shown in the form of an elongated tape, but can be in any configuration (e.g., circular, square, rectangular, etc.).

Figure 6:
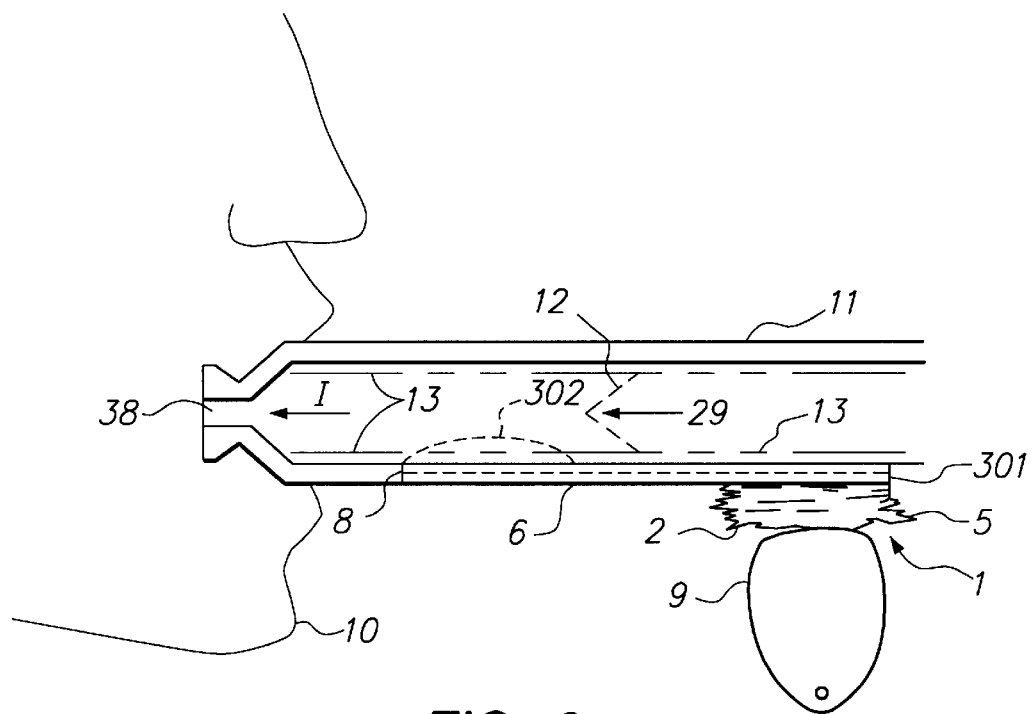
FIG. 6 is a cross-sectional view of the container of FIG. 2 in use in a channel of an aerosol delivery device.

FIG. 6 is a cross-sectional view of the disposable container 1 of FIG. 2 in use for respiratory therapy. The wall 2 is being compressed by a mechanical component such as the cam 9 shown in FIG. 9. The cam may be driven by a motor connected to gears which turn the cam 9 to bring the cam into contact with and apply the necessary force to the collapsible wall 2 of the container 1. The formulation 5 is forced through the low resistance filter 301, if present, into the open channel 6 (breaking the abutment 7 shown in FIG. 2), and against and through the nozzle 302 causing the porous membrane of the nozzle 302 to protrude outward into a convex configuration as shown in FIG. 3. The cam 9 has been forced against the container wall 2 after a patient 10 begins inhalation in the direction of the arrow "I."

An exemplary method for using the aerosol delivery device 40 is as follows. The patient 10 inhales through the mouth from a tubular channel 11. The velocity of the air moving through the flow path 29 of the channel 11 can be measured across the diameter of the channel to determine a flow profile 12, i.e., the air flowing through the channel 11 has a higher velocity further away from the inner surface of the channel. The air velocity immediately adjacent to the inner surface of the channel 11 (i.e., infinitely close to the surface) is very slow (i.e., approaches zero). A flow boundary layer 13 defines a set of points below which (in a direction from the channel center toward the inner surface of the channel) the flow of air is substantially below the bulk flow rate, i.e., 50% or less than the bulk flow rate.

As shown in FIG. 6, the convex shape that the flexible porous membrane of the nozzle 302 takes on during use plays an important role. Preferably, the upper surface of the flexible porous membrane of the nozzle 302 is substantially flush with (i.e., in substantially the same plane as) the inner surface of the channel 11 to allow air to flow freely. Thus, if the membrane of the nozzle 302 remained in place when the formulation 5 moved through the pores, the formulation would be released into the slow moving or substantially "dead air" below the boundary layer 13. However, when the formulation 5 is forced from the container 1 by force applied from a source such as a motor-driven cam 22, the formulation 5 presses against the flexible porous membrane of the nozzle 302 causing the porous membrane to convex outward beyond the plane of the resting surface of the nozzle's membrane 302 and beyond the plane of the inner surface of the channel 11. The convex upward distortion of the membrane of the nozzle 302 is important because it positions the pores of the membrane beyond the boundary layer 13 (shown in FIG. 6) into faster moving air of the channel 11.

Figure 9:
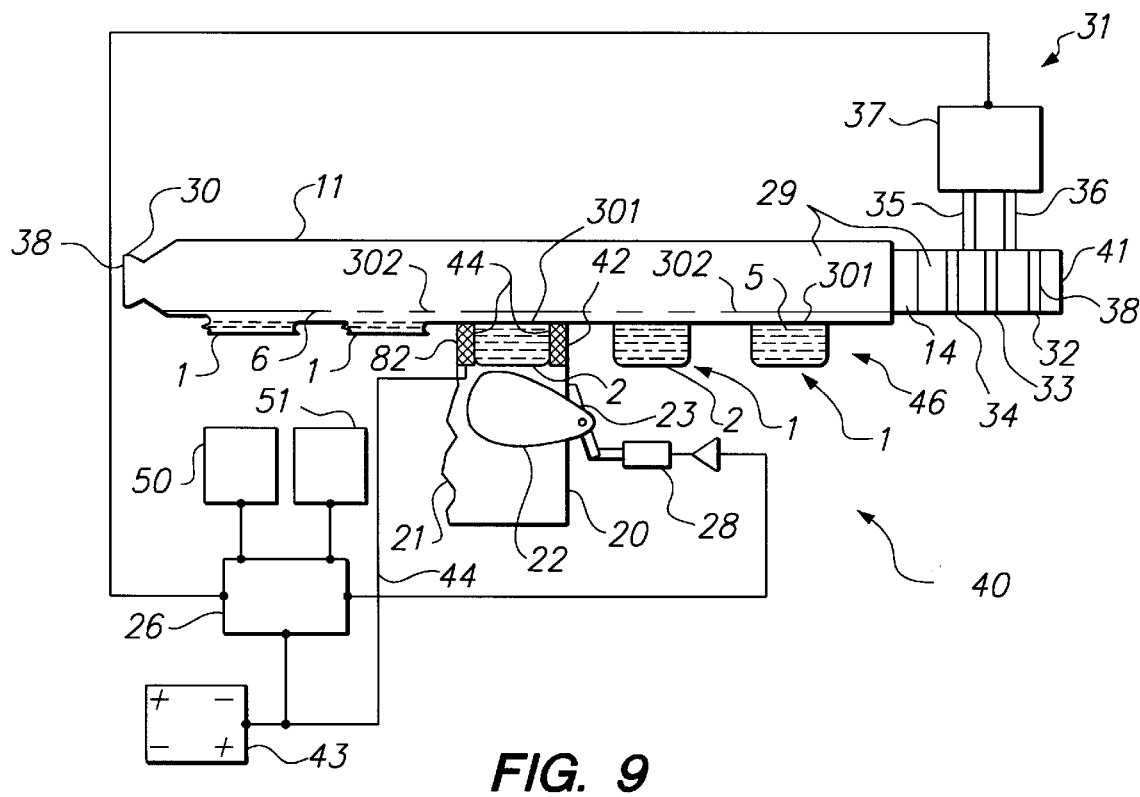
FIG. 9 is a cross-sectional view of an aerosol delivery device of the invention.
Figure 7:
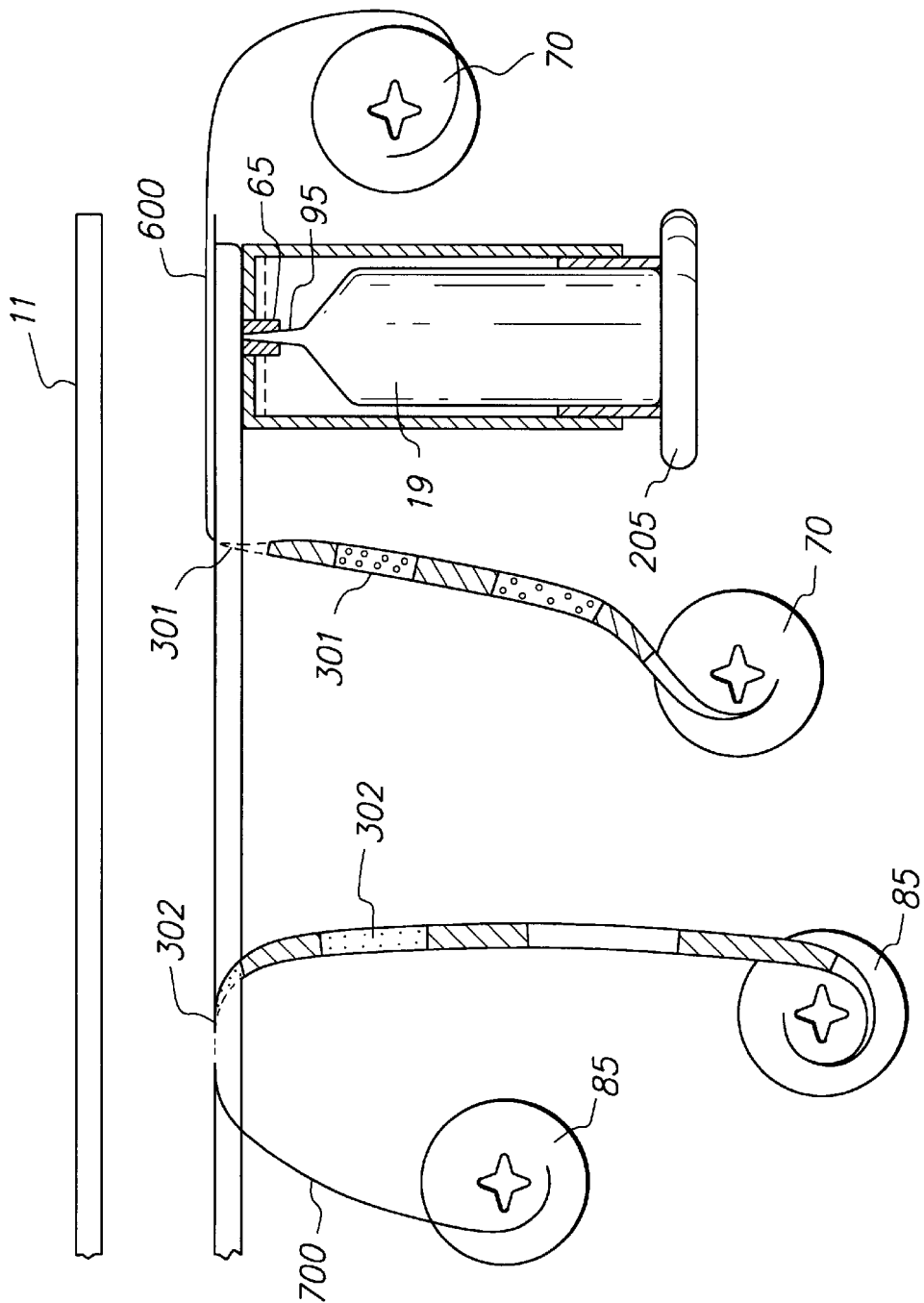
FIG. 7 is a cross-sectional view of an aerosol delivery device of the invention having a multidose container and a ribbon of low resistance filters and a ribbon of porous membranes.
Figure 8:
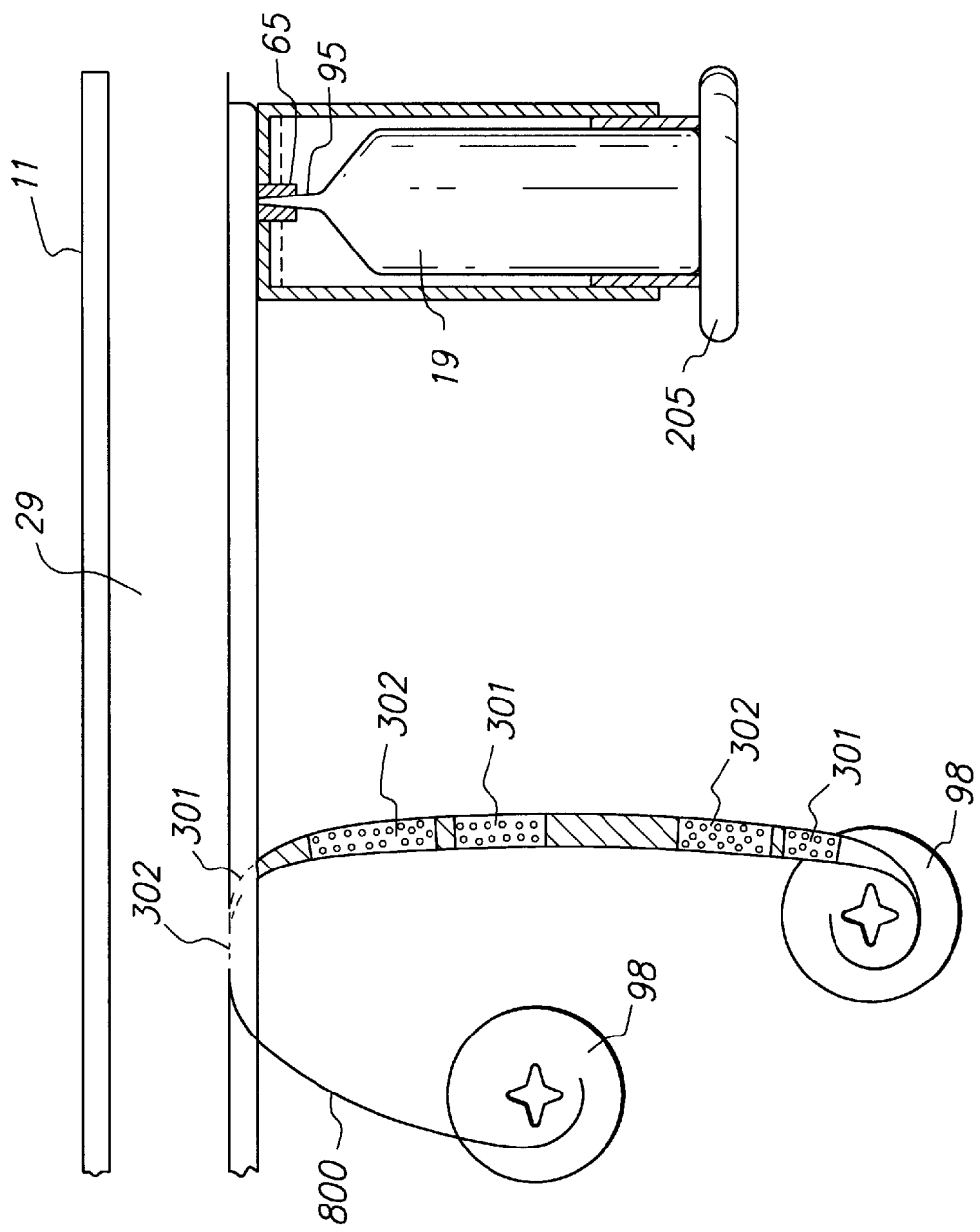
FIG. 8 is a cross-sectional view of an aerosol delivery device of the invention having a multidose container and single ribbon having both interconnected low resistance filters and nozzles comprised of porous membranes.

A device similar to the device 40 of FIG. 9 can be similarly used to deliver a drug to the respiratory tract by nasal delivery. For example, the mouthpiece 30 and opening 38 are suitably modified to provide for delivery by nasal inhalation. Thus, the patient places the opening of the modified device into his nostril and, after inhalation, a dose of the drug is delivered to the respiratory tract of the patient in a manner similar to that described above.

Aerosol delivery of a drug to the eye can be accomplished using a device similar to the device 40 described above, with modifications. For example, the device 40 shown in FIG. 9 is modified such that the mouthpiece 30, opening 38, and channel are suitable for aerosol delivery to the surface of the patient's eye. The patient positions the device so that aerosol formulation exiting the opening 38 will contact the eye's surface; the channel is open at the opening end (opening 38) and is preferably closed at the end opposite the opening end. The device may additionally comprise a means to maintain the device in a stable position over the patient's eye and/or a means for detecting when the patient's eye is open. Upon activation of the device, a cam 9 (or other mechanical component) crushes the collapsible wall 2 of the container 1. The formulation 5 is forced through the filter 301, into the open channel 6 (breaking the abutment 7), and against and through the nozzle 302, thereby generating an aerosol which is forced out of the device through an opening so as to come into contact with the surface of the eye.

The device of the invention can use a low resistance filter and a porous membrane to prevent clogging of the nozzle's porous membrane and to prevent the passage of undissolved particles or drug and/or other undesirable particles from being delivered to the patient. In general, the formulation is released from a container, passed through at least one low resistance filter, and then passed through a porous membrane of a nozzle. An aerosol is formed from the drug formulation when it exits the pores of the porous membrane, and the aerosol is delivered to the patient.

A low resistance filter and the nozzle can be included as components of a disposable package that is composed of a container that serves as a storage receptacle for the drug formulation, a porous membrane, and a low resistance filter positioned between the drug formulation and the nozzle. Such packages and containers are as described above.

The low resistance filter and the nozzle can also be provided separate from the drug container and/or the disposable package. For example, the low resistance filter can be provided as a single disposable filter that can be inserted in the proper position between the formulation in the container and a nozzle, which can also be provided as a single disposable unit. The disposable filter and disposable nozzle can be inserted prior to use and can be disposed after each use or after a recommended number of uses.

Alternatively, the low resistance filter and nozzle can be provided as a separate ribbon or ribbons.

The formulation may be a low viscosity liquid formulation. The viscosity of the drug or diagnostic agent by itself or in combination with a carrier is not of particular importance except to note that the formulation must have characteristics such that the formulation can be forced out of openings to form an aerosol, e.g., when the formulation is forced through the flexible porous membrane it will form an aerosol preferably having a particle size in the range of about 0.1 to 12 microns for intrapulmonary delivery or in the range of 15 to 75 microns for ocular delivery.

AEROSOL DELIVERY DEVICES:

In general, aerosol delivery devices useful with the invention comprise (a) a device for holding a formulation-containing container, preferably a disposable container, with at least one but preferably a number of containers, and (b) a mechanical mechanism for forcing the contents of a container (on the package) through a low resistance filter and a nozzle comprised of a porous membrane. Where the device is used for respiratory delivery, the device can further comprise (c) a means for controlling the inspiratory flow profile, (d) a means for controlling the volume in which the drug or diagnostic agent is inhaled, (e) a switch for automatically releasing or firing the mechanical means to release a determined volume of aerosol and aerosol-free air when the inspiratory flow rate and/or volume reaches a predetermined point, (f) a means for holding and moving one package after another into a drug release position so that a new package is positioned in place for each release of drug, and (g) a source of power, e.g., spring, or conventional batteries or other source of electric power.

The aerosol delivery devices of the invention can also comprise additional components such as, but not limited to, a monitor for analyzing a patient's inspiratory flow (e.g., a flow sensor 31 as shown in FIG. 9 having tubes 35 and 36 connected to a pressure transducer 37, which tubes 35 and 36 communicate with the flow path 29 and which pressure transducer is electrically connected to a microprocessor 26), a heating mechanism for adding energy to the air flow into which the aerosol particles are released (e.g., a heating mechanism 14 as shown in FIG. 9), means for measuring ambient temperature and humidity (e.g., a hygrometer 50 and thermometer 51 as shown in FIG. 9), screens to prevent undesirable particles in the environment from entering the flow path (e.g., screens 32, 33, and 34 as shown in FIG. 9), and/or other components that might enhance aerosol delivery and/or patient compliance with an aerosol delivery regimen. The device can also comprise components that provide or store information about a patient's aerosol delivery regimen and compliance with such, the types and amounts of drug delivered to a patient, and/or other information useful to the patient or attending physician. Devices suitable for aerosol delivery according to the invention (i.e., that can be adapted for use with a low resistance filter and nozzle as described herein) are described in U.S. Pat. No. 5,544,646, issued Aug. 13, 1996; U.S. Pat. No. 5,497,763, issued Mar. 12, 1996; PCT published application WO 96/13292, published May 9, 1996; and PCT published application WO 9609846, published Apr. 4, 1996, each of which is incorporated herein by reference with respect to such aerosol delivery devices.

The methodology of the present invention can be carried out with a device that obtains power from a plug-in source; however, the device is preferably a self-contained, portable device that is battery powered. For example, the methodology of the invention can be carried out using a portable, hand-held, battery-powered device which uses a microprocessor (e.g, as the means for recording a characterization of the inspiratory profile) as per U.S. Pat. No. 5,404,871, issued Apr. 11, 1995, and U.S. Pat. No. 5,450,336, issued Sep. 12, 1995, incorporated herein by reference. The microprocessor is programmed using the criteria described herein using the device, dosage units, and system disclosed in PCT Application US94/05825 with modifications as described herein. Alternatively, the methodology of the invention can be carried out using a mechanical (nonelectronic) device. Those skilled in the art would recognize that various components can be mechanically set to actuate at a given inspiratory flow rate and at a given volume (e.g., a spinnable flywheel which rotates a given amount per a given volume).

Figure 10:
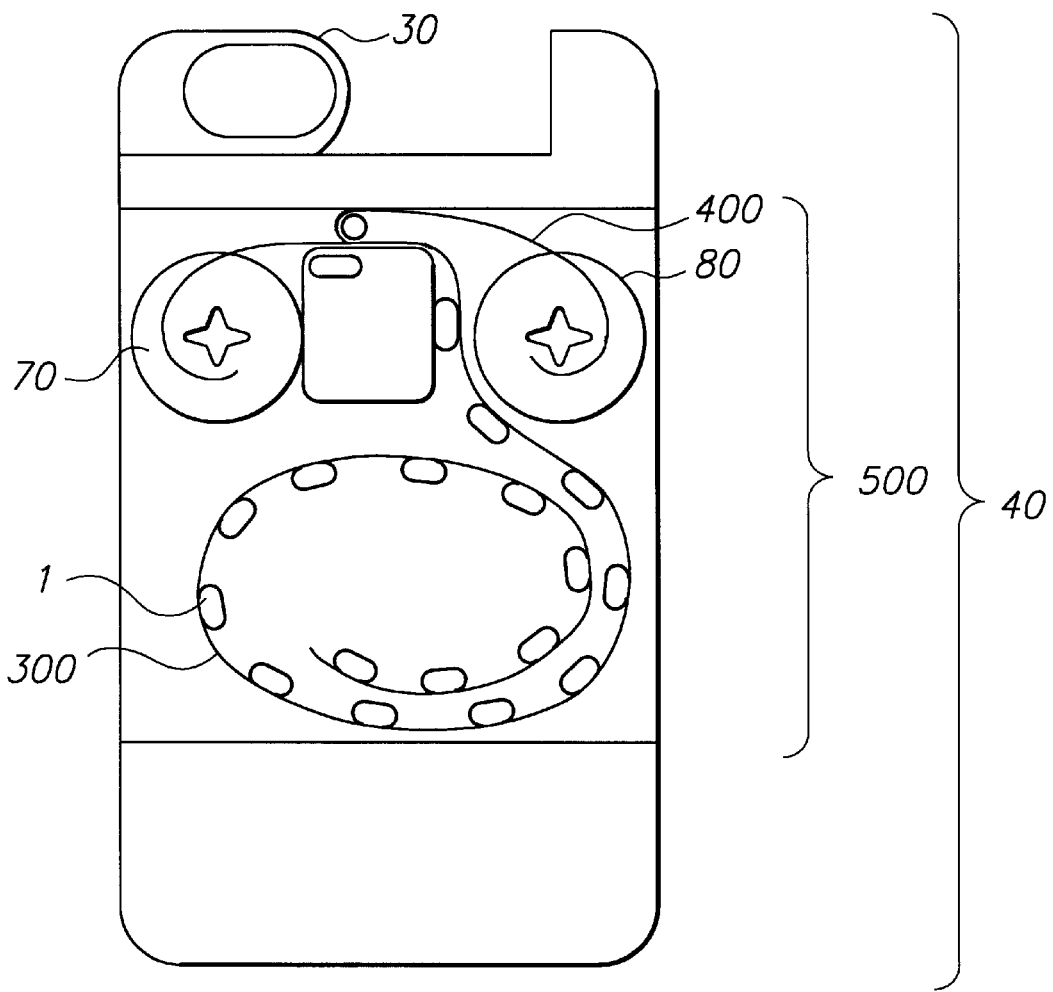
FIG. 10 is a cross-sectional view of an aerosol delivery device of the invention loaded with a cassette.
Figure 11:
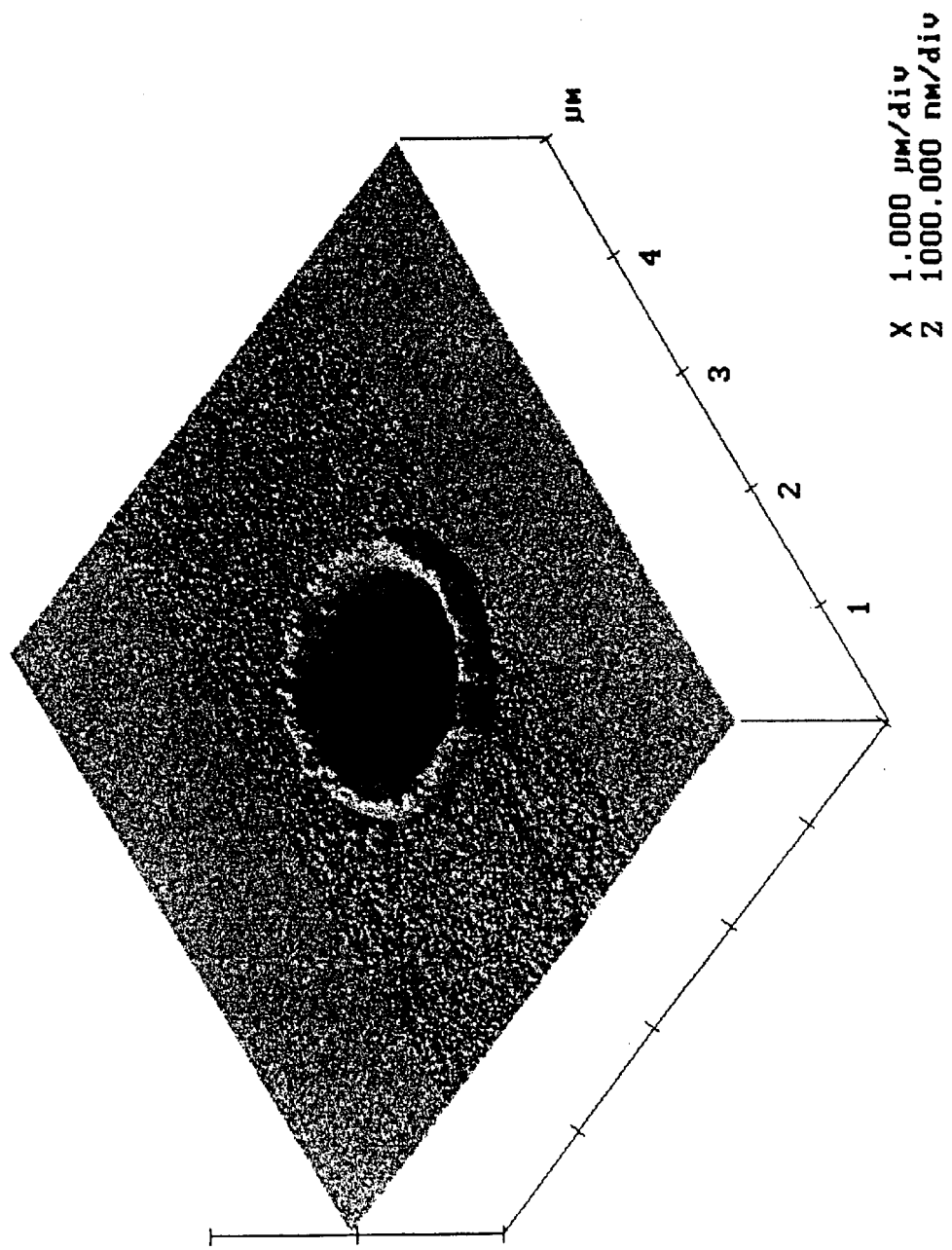
FIG. 11 is a scanning electron micrograph of the exit aperture of a pore formed by the methodology of the present invention so as to have an elevated area surrounding the exit aperture to prevent intrusion of the formulation back into the pore.

An exemplary device 40 of the invention is shown in FIG. 9. The device 40 is a hand held, self-contained, portable, breath-actuated inhaler device 40 having a holder 20 with cylindrical side walls and a hand grip 21. The holder 20 is "loaded," i.e., connected to a container 1 that includes dosage units having liquid, flowable formulations of pharmaceutically active drug or diagnostic agent therein. A plurality of containers 1 (2 or more) are preferably linked together to form a package 46. FIG. 10 is a cross-sectional view of a cassette 500 loaded into a delivery device 40. The disposable package 46 (as depicted in FIG. 9) is folded or wound into the cassette 500 in a manner which makes it possible to move the individual containers 1 into a formulation release position within the device 40. While the containers 1 are moved into position the cover 400 is removed. Although it is possible to rewind any used portion of the package on a sprocket 70 and rewind the used cover 400 on a sprocket 80 or randomly fold it into a compartment, it is also possible to dispense the used portion outside of the cassette 500 and device 40 and immediately dispose of such.

It is to be understood that while the invention has been described in conjunction with the preferred specific embodiments thereof, that the foregoing description as well as the examples which follow are intended to illustrate and not limit the scope of the invention. Other aspects, advantages and modifications within the scope of the invention will be apparent to those skilled in the art to which the invention pertains.

All patents, patent applications, and publications mentioned herein are hereby incorporated by reference in their entirety.

EXAMPLES

Example 1

PREPARATION OF NOZZLES

Nozzles were prepared from thin-film polyimide (25 $\mu$m, Kapton™ Type 100H, DuPont) using a laser (Uniphase, model s355B-100Q). The film was held by a vacuum platen to a three axis stage.

To determine the effect of power level and number of pulses on pore size, the power and pulse number was varied in a systematic fashion as pores were drilled in a single piece of Kapton. A second order polynomial fit of the pore size vs. power level was performed, and was used to estimate the power required to drill pores of diameter 1, 1.5, and 2 $\mu$m. Sample nozzles were fabricated at various power levels, and pores on each sample were sized, and the average size computed. This process was iterated until a power level was determined that gave an average pore size within 5% of the desired value.

TABLE I

Power Level vs Pore Size

| Desired Pore Size | Power Level Used |
| --- | --- |
| 1.0 $\mu$m | 1.1 mW |
| 1.5 $\mu$m | 1.5 mW |
| 2.0 $\mu$m | 1.9 mW |

Nozzles for the experiments below were fabricated at these settings. The power was checked and adjusted after every 10 nozzles.

To determine pore size, nozzles were imaged using a scanning electron microscope (Philips, model 505). The samples were coated by gold deposition (Denton Desk II, 45 $\mu$A, 120 seconds) prior to imaging. The images were digitized at video resolution using a frame grabber (Data Translation DT3152). Video frames (64) were averaged to create a final image, which was stored to disk. After 10 images had been acquired in this manner, they were read into an image processing software package (Optimus, version 6.0). A macro was developed that determined the perimeter of the pores by thresholding, and based on this perimeter, an area equivalent diameter was calculated. The area equivalent diameter determined for the 10 pores was averaged to determine the final diameter.

Example 2

Nozzles prepared as described in Example 1 were tested for generated MMAD (median size of generated aerosol), $\sigma_g$ (dispersion of the generated aerosol size distribution), and emitted dose. The nozzles were applied to AER$_x$ system disposable packages, as described in U.S. Pat. No. 5,544,646 (incorporated herein by reference), and loaded into an AER$_x$ inhaler. Nominal values for the experiment were airflow=70 liters per minute.

The MMAD of the particles prior to evaporation was measured by phase Doppler particle sizing (Aerometrics, RSA, XMT 1145, RCV 2100). Phase Doppler particle sizing uses a laser beam to scatter light from spherical aerosol particles. The scattered light is detected and analyzed to determine the particle size and velocity distribution.

The Aerometrics system was first calibrated using polystyrene latex microspheres (Duke Scientific 4205A). The particles were suspended in water, launched with a jet nebulizer (Hudson RCI, UpDraft II), and dried prior to introducing them into the probe volume. After calibration, the test aerosol was launched using an AER$_x$ system. The edge of the clamp was placed about 1.5" from the probe volume, with the plume centered on the probe volume, using nozzles of the sizes prepared in Example 1. The index of refraction used for calculations was 1.33.

Emitted dose was measured by collecting the aerosol from a single administration onto a 47 mm glass fiber filter (61631, Gelman Sciences). The aerosol was drawn from the AER$_x$ system into a tapered section which fit tightly into a 90° glass twin impinger throat (Erweka Corp., part no. 007-04), attached to the filter holder.

We found emitted doses of about 65% or greater are obtained by using pores of 1 μm diameter, using a 1.2 second extrusion time. Four of the runs (7%) exceeded 80% emitted dose, and 20 runs (37%) exceeded 60% emitted dose.

The measured MMAD ranged from 8.70 μm to 4.37 μm, while $\sigma_g$ was essentially constant over the experimental range.

Example 3

Purpose:
To determine the effect of variable exit hole size on the emitted dose and aerosol quality obtained with Excimer Nozzles.

The nozzle lots used in this experiment were designed to have exit hole sizes of approximately 0.8–1.5 μM.

ED, MMAD, GSD and FPD results were measured.

ED—fraction of the loaded dose that is emitted from the device

MMAD—mass median aerodynamic diameter

GSD—geometric standard deviation

FPD—fine particle dose (fraction of the dose loaded in the jacket that exits the mouthpiece in particles<3.5 μM aerodynamic diameter Packet Preparation: the nozzles were drilled using a UV excimer laser. After scanning electron microscopy (SEM) to examine a portion of the nozzles, the remaining nozzle file was sealed to blister jackets. The test liquid was 45 μl of cromolyn sodium (30 mg/ml) aqueous solution.

SUMMARY PERFORMANCE DATA

| SEM exit hole size (μm) from different sub-lots | ED (%) | MMAD (μm) | GSD |
|---|---|---|---|
| 1.32 ± 0.05 | 72.3 ± 3.9 | 2.51 | 1.48 |
| 1.45 ± 0.08 | | | |
| 1.20 ± 0.1 | 68.2 ± 1.5 | 2.68 | 1.44 |

-continued

SUMMARY PERFORMANCE DATA

| SEM exit hole size (μm) from different sub-lots | ED (%) | MMAD (μm) | GSD |
|---|---|---|---|
| 1.38 ± 0.05 | | | |
| 1.40 ± 0.05 | 73.4 ± 6.1 | 2.60 | 1.41 |
| 0.51 ± 0.13 | 67.13 ± 6.95 | 1.67 | 1.39 |
| 0.81 ± 0.09 | 72.04 ± 2.72 | 2.38 | 1.41 |
| 0.82 ± 0.16 | 75.96 ± 6.9 | 2.20 | 1.44 |

Figure 12:
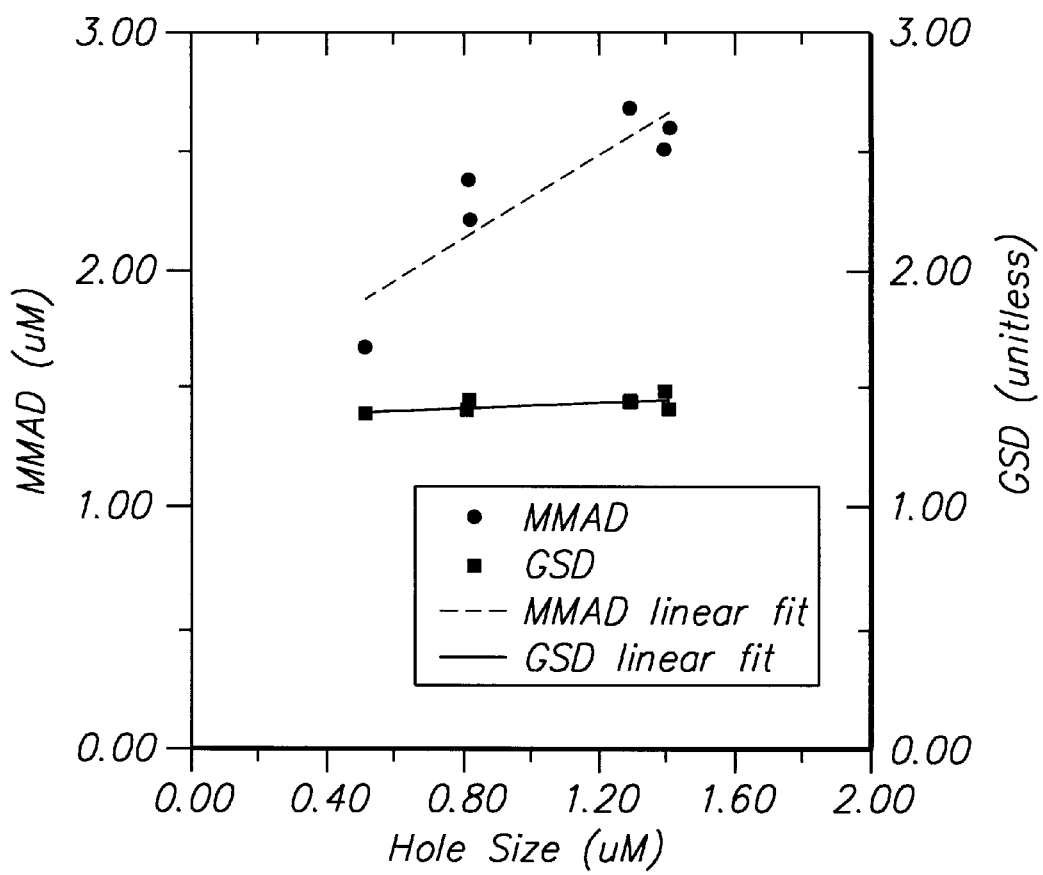
FIG. 12 is a graph of the aerosol quality vs. pore size for porous membranes generated by the method of the present invention.

FIG. 12 shows that MMAD increases with hole size as expected.

What is claimed is:

1. A nozzle for aerosolizing a drug formulation, comprising:
 a sheet of flexible membrane material having a nozzle area which area has a plurality of pores therein wherein the pores have an unflexed exit aperture diameter in the range of about 0.5 to about 50 microns which pores are positioned at a distance in the range of about 30 to about 70 microns apart from each other.

2. The nozzle of claim 1, wherein the pores are formed so that a layer of material covers the exit aperture, wherein said pores bursts outward upon application of a pressure that does not otherwise rupture the nozzle.

3. The nozzle of claim 1, wherein the exit aperture of said pores is surrounded by an elevated area.

4. The nozzle of claim 3, further comprising:
 a removable cover sheet connected to the sheet of membrane material, the cover sheet being attached in a manner which covers at least the area with pores therein.

5. The nozzle of claim 3, wherein the flexible membrane material has a thickness in the range of about 15 to 40 microns.

6. The nozzle of claim 5, wherein the flexible membrane material thickness is in the range of about 20 to 30 microns.

7. The nozzle of claim 6, wherein the flexible membrane material thickness is about 25 microns.

8. The nozzle of claim 3, wherein the nozzle area with pores therein has 100 or more pores.

9. The nozzle of claim 8, wherein the nozzle area with pores therein has 200 or more pores.

10. The nozzle of claim 3, wherein the pores are regularly spaced in the area in rows.

11. The nozzle of claim 3, wherein the flexible membrane material is a polymer selected from the group consisting of polyimides, polyether imides, polyethers, polyesters, polyethylene and polycarbonates.

12. The nozzle of claim 3, wherein the pores are conical.

13. The nozzle of claim 3, wherein said nozzle comprises a plurality of nozzle areas.

14. A method of generating an aerosol, comprising forcibly applying a flowable liquid formulation to the nozzle of claim 3.

15. A method of delivering a drug or diagnostic agent to an individual, comprising:
 forcibly applying a liquid comprising the drug or diagnostic agent to the nozzle of claim 2 so that an aerosol containing the drug or diagnostic agent is generated; and
 administering the aerosol to an area of the individual in a pharmaceutically acceptable and effective manner.

16. A disposable package for use in aerosolized delivery of drugs to the lung, comprising:

a container having at least one wall which is collapsible by the application of a force and having at least one opening; and a nozzle covering the opening of the container, wherein the nozzle is comprised of a sheet of flexible membrane material having a nozzle area which area has a plurality of pores therein, wherein the pores have an unflexed exit aperture diameter in the range of about 0.5 to 50 micron which pores are positioned at a distance in the range of about 30 to 70 microns apart from each other.

17. The disposable package of claim 16, wherein the opening leads to an open channel and the nozzle is positioned at the end of the open channel.

18. The package of claim 17, wherein a filter is positioned in the open channel.

19. A disposable package for use in aerosolized delivery of material to a lung, comprising:

a container having at least one wall which is reversibly collapsible by the application of force and having at least one opening; and a porous membrane covering the opening wherein the membrane pores have an unflexed exit aperture diameter in a range of about 0.5 to about 5.0 microns, and wherein the pores are configured to have an elevated area surrounding the exit aperture of the pore.

20. The disposable package of claim 19, wherein the elevated areas are formed as an integral part of the membrane as elevated areas on the membrane prior to forming pores at the center of the elevated areas.

21. The disposable package of claim 19, wherein the elevated areas are formed by a thin membrane layer at an end of a partially formed pore which thin membrane layer is broken as material is forced out.

22. The disposable package of claim 19, wherein the elevated areas are formed by depositing elevated areas on the membrane and making pores in the membrane through the elevated areas.

23. The disposable package of claim 19, wherein the elevated areas are formed by etching away surrounding areas to leave elevated areas on the member and making pores through the elevated areas.

24. A disposable package for use in aerosolized delivery of material to lungs, comprising:

a container having at least one wall which is collapsible by the application of force and having at least one opening, the container having therein a liquid, flowable formulation; and a membrane covering the opening wherein the membrane comprises a plurality of substantially circular weakened areas having an unflexed diameter in a range of about 0.5 to about 5.0 microns which weakened areas burst when pressure is applied while the remainder of the membrane remains unbroken.

* * * * *